United States Patent [19]

Arakawa

[11] Patent Number: 4,616,630
[45] Date of Patent: Oct. 14, 1986

[54] ENDOSCOPE WITH AN OBTUSELY ANGLED CONNECTING SECTION

[75] Inventor: Satoshi Arakawa, Omiya, Japan

[73] Assignee: Fuji Photo Optical Co., Ltd., Japan

[21] Appl. No.: 766,413

[22] Filed: Aug. 16, 1985

[30] Foreign Application Priority Data

Aug. 20, 1984 [JP] Japan .............................. 59-126264[U]
Aug. 20, 1984 [JP] Japan ........................ 590-126265[U]

[51] Int. Cl.⁴ ............................................... A61B 1/00
[52] U.S. Cl. ........................................................ 128/4
[58] Field of Search ...................... 128/4, 6; 273/148 B

[56] References Cited

U.S. PATENT DOCUMENTS

| | | | |
|---|---|---|---|
| 4,384,570 | 5/1983 | Roberts | 128/4 |
| 4,475,539 | 10/1984 | Konomura | 128/6 |
| 4,517,962 | 5/1985 | Heckele | 128/6 |
| 4,566,437 | 1/1986 | Yamaguchi | 128/4 |

Primary Examiner—William H. Grieb
Attorney, Agent, or Firm—Parkhurst & Oliff

[57] ABSTRACT

An endoscope used for observing the interior of a cavity in a human body. The endoscope according to the present invention is provided in the forward end of an insertion section with an image sensor and an object of interest can be displayed on a screen of a television set in response to a video signal obtained from the image sensor. In this endoscope according to the present invention, a main body of a control section includes a grip section and a connecting section projecting at an obtuse angle forwardly and downwardly from this grip section, so that, when the endoscope is operated, such troublesomeness can be avoided that the connecting section interferes with an operator's body. Furthermore, a control button or buttons of the endoscope are provided on the front surface or the rear surface, so that the control button or buttons can be easily operated by an index finger or a thumb.

5 Claims, 5 Drawing Figures

ENDOSCOPE WITH AN OBTUSELY ANGLED CONNECTING SECTION

BACKGROUND OF THE INVENTION

1. Field of the Invention

This invention relates to endoscopes, and more particularly to an endoscope wherein a solid state imaging device is provided at the forward end of an insertion portion and an object of interest is displayed for the observation on a television screen and the like in response to a video signal obtained from the solid state imaging device.

2. Description of the Prior Art

Many of the conventional endoscopes have been constructed such that an objective lens and an eyepiece lens are disposed at opposite end portions of an image transmission optical fiber bundle, an image of an object of interest is made to focus at an end face of the optical fiber bundle through an objective lens, and the image which is transmitted through the optical fibers and appearing at the opposite end face is observed through the eyepiece lens. More specifically, as shown in FIG. 1, the conventional endoscope comprises a main body 10 of control section, a flexible insertion section 12 to be connected to this main body 10 of control section, to be inserted into a very deep portion of a living body or the like, and a cable 16 as being a connector section for connecting a control unit 14 incorporating various control mechanisms including a light source necessary for the endoscope and others to the main body 10 of control section.

In such fiberoptic endoscopes as having an image transmission optical fiber bundle for transmitting an optical image of an object, which is observed through an eyepiece lens, the main body 10 of control section comprises a grip section which can be necessarily grasped by one hand of an operator and an eyepiece section 17 disposed upwardly of this grip section and on the uppermost end of the control section 10. More specifically, as shown in FIG. 2, a grip section 10A connected to the rear end of an insertion section 12 is formed at the lower end portion of the main body 10 of control seciton, and further, an eyepiece section 17 including an eyepiece lens is provided on the top portion of the main body 10 of control section. Provided on the front face of the main body 10 of control section are a first control button 18 for air and water supply and a second control button 20 for suction. With the above-described arrangement, in the control section of the endoscope, as shown in FIG. 2, the operator grasps the grip section 10A of the main body 10 of control section with a middle finger 22A, a third finger 22B and a little finger 22C of his left hand and operates the first or second control button 18 or 20 with an index finger 22D, while looking into the eyepiece section 17.

However, when using the conventional endoscope shown in FIGS. 1 and 2, to look into the eyepiece section 17, the operator is required to bring the main body 10 of control section close to his face by raising his arm, otherwise to bring his head close to the eyepiece section 17 by bending his body forward. Therefore, the operator will be obliged to assume an unnatural posture, undesirably resulting in that his arm, waist and the like become numb after a long period of the observation.

Recently, on the other hand, there has been proposed an endoscope of the type, wherein a solid state imaging device such as a charge coupled device (CCD) or a metal oxide silicon (MOS) image sensor is provided at the forward end of the insertion section of the endoscope, and a video signal of the object of interest obtained from this solid state imaging device is displayed on a screen of a monitor television or the like, so that the object can be observed. Because of such endoscope as described above, different from a conventional endoscope which is adapted to form an image transmitted through the optical fibers for observation or inspection, it has the advantage of the preparation of no eyepiece section 17 and of reduced fatigue during the handling for long period of time and of the provision of the control section having a form of easy handling. Furthermore, there is no need for the operator to look into the eyepiece section 17, whereby the degree of freedom in changes of posture of the control section is increased. Therefore, as for the cable 16 connecting the control section 10 to the control unit 14, it is desirable to adopt a positional arrangement not interfering the operations as far as possible.

SUMMARY OF THE INVENTION

The present invention has been developed to obviate the above-described disadvantages of the prior art and has as its object the provision of an endoscope wherein fatigue is low in use for a long period of time, handling of the control buttons in the control section is easy, and the cable connecting the control section to the control unit does not interfere with the operator during his operation.

According to the present invention, a main body of a control section of the endoscope is constituted by an elongate grip section grasped by fingers other than a thumb and a connecting section obliquely downwardly projecting from the front surface of the bottom end portion of this grip section and having a center axis A making an obtuse angle $\theta$ ($90° < \theta < 180°$) with a center axis B of the grip section and being connected to the rear end of the insertion section on the same axial line, so that the operator can grasp the main body of control section easily and in an easy posture, with reduced fatigue in use for a long period of time. Furthermore, according to the present invention, a control button or buttons are disposed within an angular scope of $\theta/2$ forwardly from the center axis B of the grip section on the front surface or the top surface of the main body of control section, so that the operator can easily operate the control button with his index finger, middle finger or the like. Additionally according to the present invention, the control button or buttons are disposed at positions rearwardly of the center axis B of the grip section and within a scope higher than a bisector C of an angle $\theta$ passing through an intersection O between the center axes A and B, so that the operator can easily operate the control button or buttons with his thumb.

BRIEF DESCRIPTION OF THE DRAWINGS

The exact nature of this invention, as well as other objects and advantages thereof, will be readily understood from consideration of the following specification relating to the accompanying drawings, in which like reference characters designate the same or similar parts throughout the Figures thereof and wherein.

DETAILED DESCRIPTION OF THE INVENTION

Description will hereunder be given of the preferred embodiments of an endoscope according to the present invention with reference to the accompanying drawings.

Figure 1:
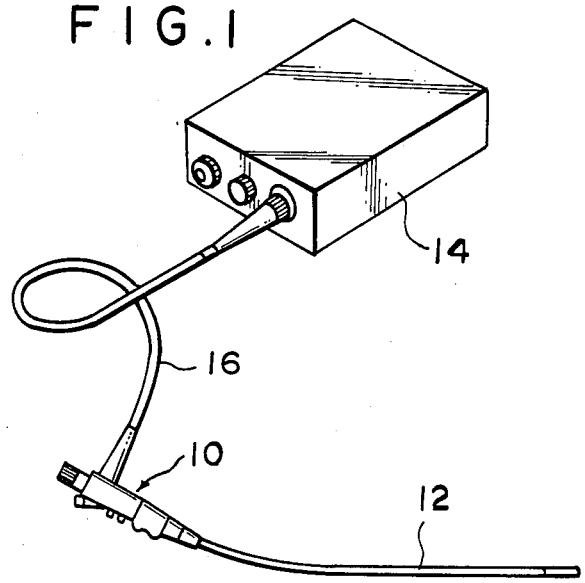
FIG. 1 is an explanatory view showing the general arrangement of the conventional endoscope.
Figure 2:
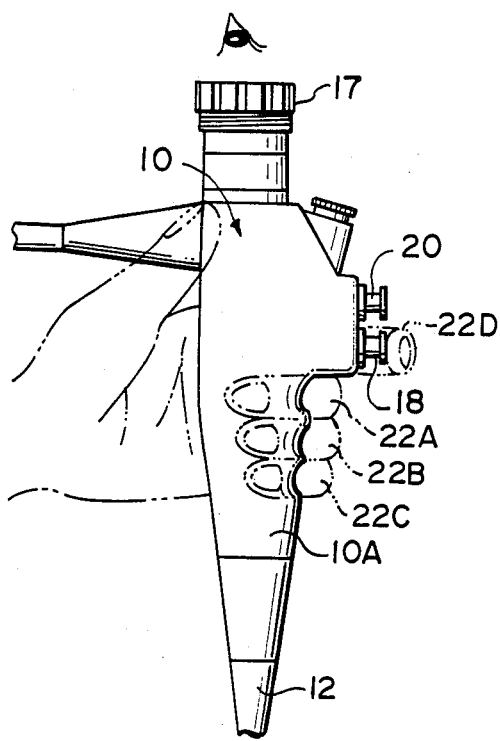
FIG. 2 is a front view showing the form of the control section of the conventional endoscope.
Figure 3:
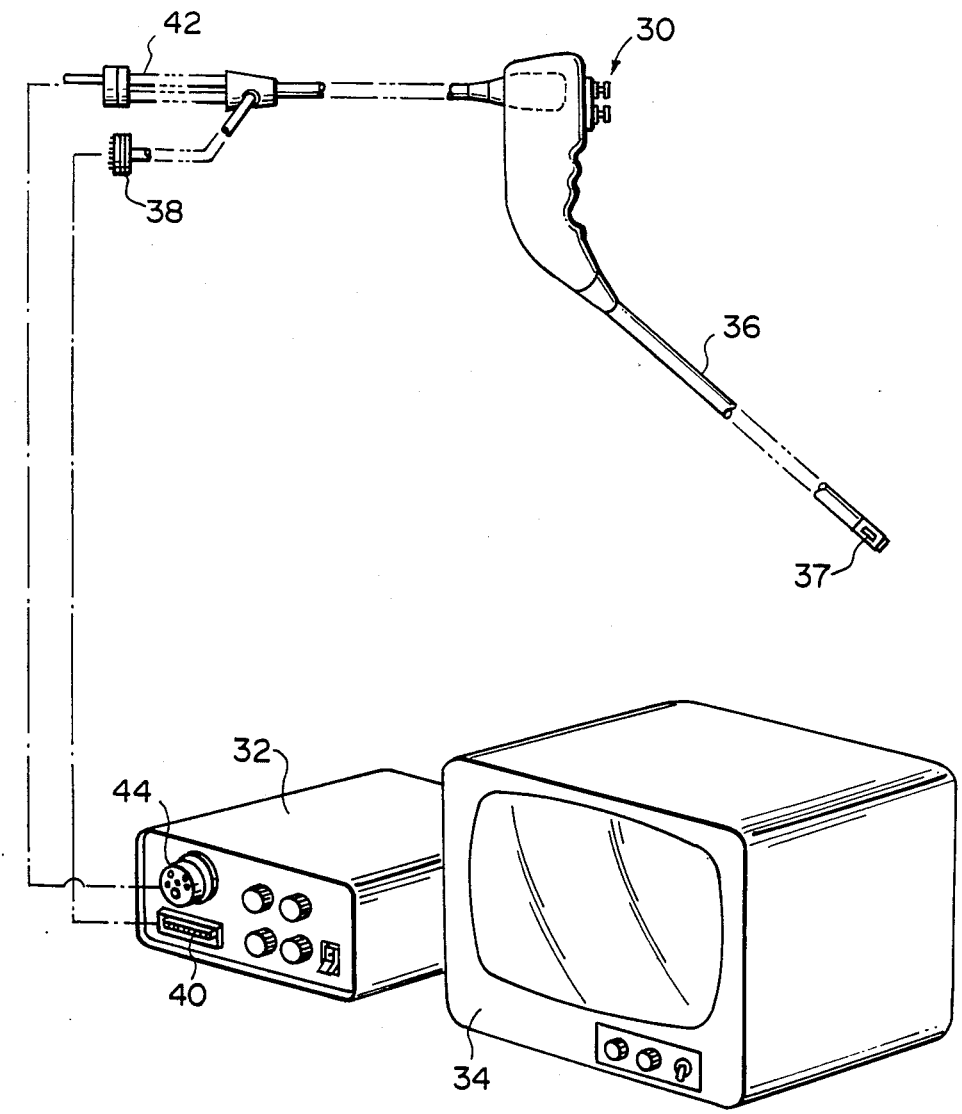
FIG. 3 is an explanatory view showing the general arrangement of the endoscope according to the present invention.

FIG. 3 shows the general arrangement of the endoscope according to the present invention. Designated at 30 is a control section, 32 a control unit and 34 a monitor television. A solid state imaging device 37 is provided at the forward end of an insertion section 36. The control unit 32 comprises a lamp for feeding light to a light guide, a process section for feeding a driving signal to the solid state imaging device 37 and processing a video signal obtained from the solid state imaging device, a power source and so on. The monitor television 34 displays an object of interest a screen in response to a video signal obtained from the solid state imaging device 37 at the forward end of the insertion section 36 through the control unit 32. Additionally, a connector 38, to which is connected a lead wire of the solid state imaging device of the endoscope, is connected to a socket 40 of the control unit 32, and a plug 42 including a light guide and the like is connected to a socket 44.

Figure 4:
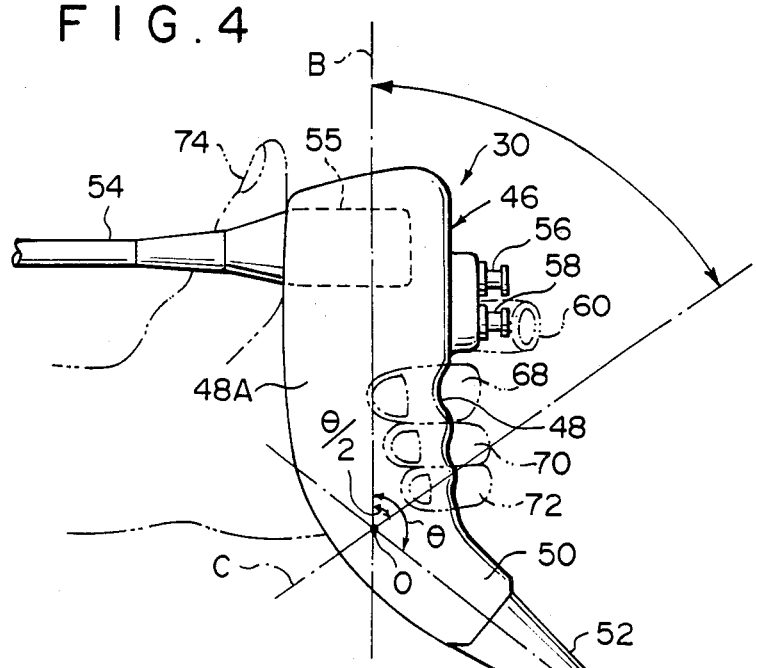
FIG. 4 is a front view showing the form of the manual control section in a first embodiment of the endoscope according to the present invention.

FIG. 4 shows the general arrangement of the control section 30 of the endoscope according to the present invention. The main body 46 of the control section 30 comprises a connector section 50 and a grip section 48. The grip section 48 is elongate, and normally, grasped for example by a middle finger, a third finger and a little finger of a left hand. A connecting section 50 being directed obliquely downwardly is integrally projected from the front surface of the bottom end portion of this grip section 48. The center axis A of this connecting section 50 makes an obtuse angle $\theta(90° < \theta < 180°)$ with the center axis B of the grip section 48, and the rear end of the insertion section 36 is connected to the forward end portion 52 of this connecting section 50 and is on the same axial line with the connecting section 50. In the insertion section 36, not shown though, there are provided a light guide composed of an optical fiber bundle, a lead wire connected to a solid state imaging device 37, an air-water supply pipe and the like. On the other hand, a connecting section 55 of a cable 54 connected to a control unit 32 is provided at a position close to the top end of one side surface (a surface where the back of the left hand of the operator is positioned) of the grip section 48, and this cable 54 substantially perpendicularly intersects the center axis B of the grip section 48 and extends rearwardly. The connecting section 55 is normally rigid and provided on one side surface of the grip section 48, whereby, even if the control section comes close to the operator's body during operation, the operator can easily operate without being interfered with the connecting section 55.

In the upper portion of the front surface of the main body of control section 46, there are provided a pair of control buttons 56 and 58 erected forwardly and arranged in the vertical direction. These control buttons 56 and 58 are used as a video tape recorder control switch (VTR·SW) button, a suction button, an air-water supply button or the like, adapted to be pushed in to control a valve device, a switch and the like, which are not shown, and the changeover from air supply to water supply or suction operation are performed in accordance with the push-in valve. These control buttons 56 and 58 are disposed at positions forwardly of the center axis B of the grip section 48 and in a scope higher than a bisector C of the obtuse angle $\theta$ passing though an intersection O between the center axis B of the grip section 48 and the center axis A of the connecting section 50. In other words, the control buttons 56 and 58 are provided within an angular scope of $\theta/2$ forwardly from the center axis B. This scope is positioned just at a portion where an indexfinger 60 is applied to the control buttons 56 and 58 when the elongate grip section 48 is grasped by the left hand.

In consequence, when the control buttons 56 and 58 are provided within the aforesaid scope, if the grip section is grasped with a middle finger 68, a third finger 70, a little finger 72 and a thumb 74 as shown, then the control buttons 56 and 58 can be very easily operated with the index finger 60.

The main body 46 of control section is provided with a control knob for angle, not shown though, this control knob rotatably drives a drum of an angle control mechanism, not shown, and linearly moves a control wire inserted into the insertion section 36, so that a direction of a curve of the forward end of the insertion section 36 including the solid state imaging device 37 can be varied.

Description will hereunder be given of action of one embodiment of the endoscope with the above-described arrangement according to the present invention. In the first place, the operator grasps the grip section 48 with the middle finger 68, the third finger 70, the little finger 72 and the thumb 74, an upper arm and a lower arm of a left arm grasping the grip section 48 are bent at a right angle to each other, the upper arm is brought into contact with the side of the operator, and a wrist portion is stabilized. In this case, the insertion section 36 projects at the angle $\theta$ (the obtuse angle) forwardly from the bottom end of the grip section 48 through the connecting section 50, so that such troublesomeness is avoided that the insertion section 36 interferes with the operator's body.

The control buttons 56 and 58 are operated with the index finger 60 when necessary, whereby the recording into the video tape recorder, the suction, the air supply, the water supply or the like is operated.

In the above embodiment, description has been given of the case where the grip section 48 has been grasped with the middle finger 68, the third finger 70, the little finger 72 and the thumb 74 and the respective control buttons 56 and 58 have been operated with the index finger 60, however, the grip section 48 may be grasped with the third finger 70 and the little finger 72, the upper control button 56 may be operated with the index finger 60, and the lower control button 58 may be operated with the middle finger 68.

Furthermore, in the above embodiment, the control buttons 56 and 58 have been provided on the front surface of the main body 46 of control section, however, these control buttons 56 and 58 may be provided on the top surface of the main body 46 of control section within the scope of allowing the index finger 60 or the middle finger 68 of the hand grasping the grip section 48 to reach.

In the above embodiment, two control buttons have been provided, however, one, or three or more control buttons may be provided.

Figure 5:
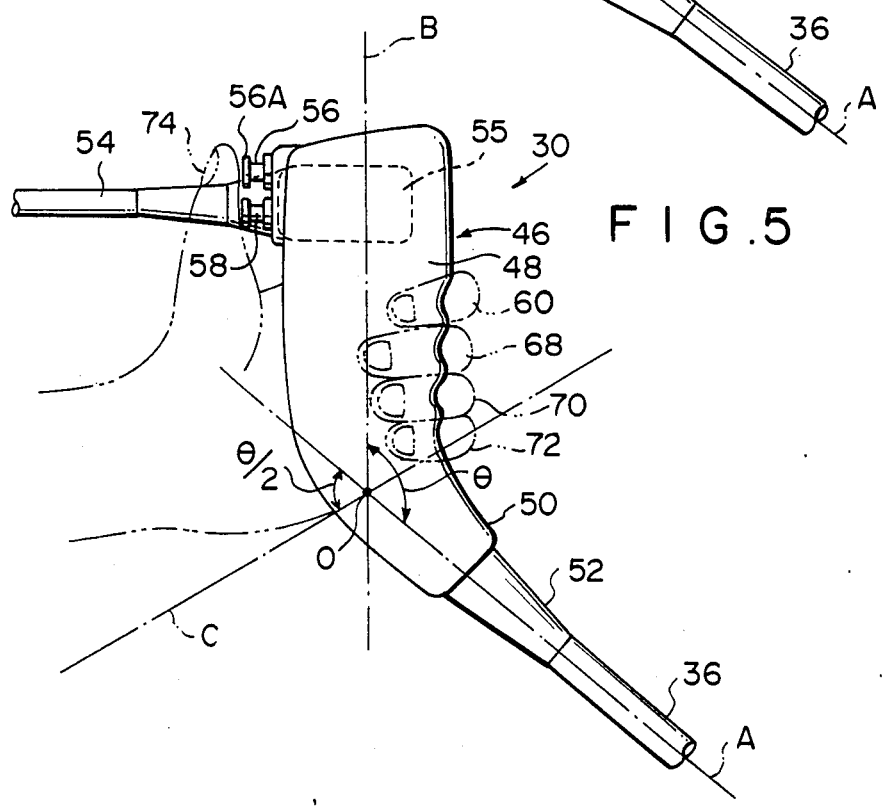
FIG. 5 is a front view showing the form of the manual control section in a second embodiment of the present invention.

FIG. 5 is a front view showing the shape of the control section in the second embodiment of the endoscope according to the present invention.

In the second embodiment shown in FIG. 5, the same or similar members to those in the first embodiment shown in FIG. 4 are depicted by the same reference numerals as the latter to avoid detailed description.

The grip section 48 is elongate, and normally, grasped with the fingers of the left hand other than the thumb. The connecting section 50 projects obliquely forwardly from the front surface of the bottom end portion of this grip section 48.

The control buttons 56 and 58 are disposed at positions rearwardly of the center axis B of the grip section 48 and within a scope higher than a straight line C indicating $\theta/2$ and passing through the intersection O between the center axis B of the grip section 48 and the center axis A of the connecting section 50. In other words, when the elongate grip section 48 is grasped with the left hand, these control knobs 56 and 58 are disposed within a scope allowing the thumb 74 to easily operate these control buttons.

In consequence, if the control buttons 56 and 58 are provided within this scope, then, when the grip section 48 is grasped with the index finger 60, the middle finger 68, the third finger 70 and the little finger 72, the operation of the control buttons 56 and 58 can be easily made with the thumb 74.

Description will hereunder be given of action of the second embodiment of the endoscope with the above-described arrangement according to the present invention. In the first place, the operator grasps the grip section 48 with the index finger 60, the middle finger 68, the third finger 70 and the little finger 72, the upper arm and the lower arm of the left arm grasping the grip section 48 are bent at a right angle to each other, the upper arm is brought into contact with the side of the operator, and a wrist portion is stabilized. In this case, the insertion section 36 projects at the obtuse $\theta$ forwardly from the bottom end of the grip section 48 through the connecting section 50, so that such troublesomeness can be avoided that the rear end of the insertion section 36 interferes with the operator's body and so forth.

The control buttons 56 and 58 are operated with the thumb 74 when necessary, whereby the recording into the video tape recorder, the suction, the air supply, the water supply or the like is operated.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope wherein a solid state imaging device is provided in the forward end of an insertion section and an object of interest is displayed on a display screen in response to a video signal obtained from said solid state imaging device, characterized in that a main body of control section of said endoscope comprises:
   an elongate grip section grasped at least by a third finger and a little finger; and
   a connecting section projecting obliquely downwardly from the front surface of the bottom end portion of said grip section, having a center axis A making an obtuse angle $\theta(90°<\theta<180°)$ with a center axis B of said grip section B and being connected to the rear end of said insertion section on the same axial line.

2. An endoscope as set forth in claim 1, wherein at least one control button is disposed within an angular scope of $\theta/2$ forwardly from the center axis B of the grip section on the front surface or the top surface of the main body of control section.

3. An endoscope as set forth in claim 1, wherein at least one control button is disposed at a position rearwardly of the center axis B of the grip section and within a scope higher than a bisector C of an angle $\theta$ passing through an intersection O between the center axes A and B.

4. An endoscope as set forth in claim 2, where in said control button or buttons include a video tape recorder control button, a suction button or an air-water supply button.

5. An endoscope as set forth in claim 2, wherein a connecting section between a control unit and a connecting cable is provided on one side surface of said grip section of the endoscope.

* * * * *